United States Patent [19]

Zhang et al.

[11] Patent Number: 5,451,405
[45] Date of Patent: Sep. 19, 1995

[54] SKIN TREATMENT COMPOSITION

[75] Inventors: Kelly H. Zhang, Piscataway; Richard Kosturko, Nutley, both of N.J.; John B. Bartolone, Bridgeport, Conn.; Anthony V. Rawlings, Wyckoff, N.J.

[73] Assignee: Chesebrough-Pond's USA Co., Greenwich, Conn.

[21] Appl. No.: 232,896

[22] Filed: Apr. 25, 1994

[51] Int. Cl.$^6$ .......................... A61K 7/00; A61K 7/48
[52] U.S. Cl. ........................ 424/401; 424/59; 514/513; 514/553; 514/557; 514/562; 514/578; 514/844; 514/847
[58] Field of Search .......................... 424/401, 59, 60; 514/513, 553, 557, 562, 578, 844, 847

[56] References Cited

U.S. PATENT DOCUMENTS

| | | | |
|---|---|---|---|
| 3,242,052 | 3/1966 | Sheffner | 167/87.1 |
| 3,591,686 | 7/1971 | Sheffner | 424/234 |
| 3,647,834 | 3/1972 | Martin | 260/429.9 |
| 3,749,770 | 7/1973 | Martin | 424/72 |
| 4,016,287 | 4/1977 | Eberhardt et al. | 424/309 |
| 4,132,803 | 1/1979 | Martin | 424/316 |
| 4,139,610 | 2/1979 | Miyazaki et al. | 424/72 |
| 4,164,570 | 8/1979 | Clough et al. | 424/175 |
| 4,276,284 | 6/1981 | Brown | 424/101 |
| 4,331,648 | 5/1982 | Myers, Jr. et al. | 424/10 |
| 4,411,886 | 10/1983 | Hostettler et al. | 424/70 |
| 4,424,234 | 1/1984 | Alderson | 514/557 |
| 4,708,965 | 11/1987 | Morgan | 514/563 |
| 4,711,780 | 12/1987 | Fahim | 424/145 |
| 4,721,705 | 1/1988 | Schreuder | 514/54 |
| 4,724,239 | 2/1988 | Morgan | 514/563 |
| 4,827,016 | 5/1989 | Morgan | 560/16 |
| 4,859,653 | 8/1989 | Morelle et al. | 514/2 |
| 4,868,114 | 9/1989 | Nagasawa et al. | 435/112 |
| 4,876,283 | 10/1989 | Reichert | 514/562 |
| 5,023,235 | 6/1991 | N'Guyen | 514/18 |
| 5,118,707 | 6/1992 | Chatterjee et al. | 514/469 |
| 5,244,665 | 9/1993 | Natraj | 424/401 |
| 5,296,500 | 3/1994 | Hillebrand | 514/562 |
| 5,314,873 | 5/1994 | Tomita et al. | 514/21 |

FOREIGN PATENT DOCUMENTS

| | | |
|---|---|---|
| 873359 | 6/1971 | Canada . |
| 0219455 | 4/1987 | European Pat. Off. . |
| 0269017 | 6/1988 | European Pat. Off. . |
| 0280606 | 8/1988 | European Pat. Off. . |
| 0304017 | 2/1989 | European Pat. Off. . |
| 0339508 | 11/1989 | European Pat. Off. . |
| 0440298 | 8/1991 | European Pat. Off. . |
| 2244541 | 4/1975 | France . |
| 2651129 | 3/1991 | France . |
| 150694 | 9/1981 | Germany . |
| 60124 | 9/1990 | Hungary . |
| 3-184922 | 8/1991 | Japan . |
| 2180153 | 3/1987 | United Kingdom . |
| 2192789 | 1/1988 | United Kingdom . |
| 2192790 | 1/1988 | United Kingdom . |
| WO93/04669 | 3/1993 | WIPO . |
| WO93/10755 | 6/1993 | WIPO . |

OTHER PUBLICATIONS

"Single Drugs-N-acetylcysteine", *Drugs of Today*, vol. 16, No. 2 (1980) pp. 41–43.

Bailey, K. R. et al., "The Reduction of Experimentally Induced Inflammation by Sulfhydryl Compounds", *Biochemical Pharmacology*, vol. 16 (1967) pp. 1175–1182.

Bartek, Methodius J. et al., "Percutaneous Absorption, In Vitro", *Animal Models in Dermatology*, (1975) pp. 103–120.

Infection, "Surgical Forum", pp. 49–50.

(List continued on next page.)

*Primary Examiner*—Gollamudi S. Kishore
*Attorney, Agent, or Firm*—Rimma Mitelman

[57] ABSTRACT

It should be understood that the specific forms of the invention herein illustrated and described are intended to be representative only. Changes, including but not limited to those suggested in this specification, may be made in the illustrated embodiments without departing from the clear teaching of the disclosure. Accordingly, reference should be made to the following appended claims in determining the full scope of the invention.

6 Claims, No Drawings

OTHER PUBLICATIONS

Kahn, Guinter, M. D., et al. "Ultraviolet Light Protection by Several New Compounds", *Arch. Dermatology*, vol. 109, Apr. 1974, pp. 510-517.

Portelli, M. et al., "Synthesis of N-acetylcysteine Compounds", *II Farmaco Edizione Scientifica*, vol. 31, No. 11, Nov. 1976, pp. 768-775.

Reyniers, P. et al., "The Evaluation of New Methods for Extraction of Keratins from Epidermis", Arch. In. Physiol. Biochem., vol. 88(3), (1980) p. B146.

Verhey, Lynn J. et al., "Determination of the Radioprotective Effects of Topical Applications of MEA, WR-2721 and N-acetylcysteine on Murine Skin". *Radiation Research*, 93, (1983), pp. 175-183.

Isom, Gary E. et al., "Targeted Drug Carriers: Biological Activity of the N-acetylcysteine-liposome System". *Methodol. Surv. Biochem. Anal.*, vol. 13 (1984), pp. 331-337.

Kligman, Lorraine H., M.D. "Effects of all-trans-retinoic Acid on the Dermis of Hairless Mice", *Journal of the American Academy of Dermatology*, vol. 15, No. 4, Pt. 2, Oct. 1986, pp. 779-785.

Rougee, M. et al., "Deactivation of Singlet Molecular Oxygen by Thiols and Related Compounds, Possible Protectors Against Skin Photosensitivity", *Photochemistry and Photobiology*, vol. 47, No. 4, (1988), pp. 485-489.

Staal, Frank J. T. et al., "Intracellular Thiols Regulate Activation of Nuclear Factor $\kappa$B and Transcription of Human Immunodeficiency Virusl", *Proc. Natl. Acad. Sci. USA*, vol. 87, Dec. 1990, pp. 9943-9947.

Karg, Eszter et al., "Alteration of Glutathione Level in Human Melanoma Cells: Effect of N-Acetyl-L-Cysteine and its Analogues", *Pigment Cell Research*, vol. 3, (1990), pp. 11-15.

"Acetylcysteine", The Merck Index, 11th Edition, p. 14., 1990.

Gillette, James H. et al., "Ornithine Decarboxylase: A Biochemical Marker of Repair in Damaged Tissue", *Life Sciences*, vol. 48, No. 16 (1991), pp. 1501-1510.

Chemical Abstract 117(26):257989e., 1992.

Abstract of FR 2 244 541. Aug. 1973.

Abstract of German Patent No. 150 694. Aug. 1981.

Gavish, D. et al. "Lipoprotein (a) reduction by N-acetylcysteine", vol. 337, Jan. 26, 1991, pp. 203-204.

Derwent Abstract of J6 1289017., Jun. 1985.

SKIN TREATMENT COMPOSITION

FIELD OF THE INVENTION

The invention relates to skin treatment compositions containing an alpha hydroxy acid or an ester or a salt thereof in combination with N-acetyl-L-cysteine, and the use of the compositions for enhancing lipid biosynthesis in mammalian skin.

BACKGROUND OF THE INVENTION

Layers of lipids in stratum corneum of the skin form a "water barrier" which prevents water loss from the skin. Known classes of stratum corneum lipids include sphingolipids, free fatty acids, sterols and sterol esters, and phospholipids, with sphingolipids being a major component. Sphingolipids, in turn, consist of four major classes of lipids: glycosphingolipids, ceramides, sphingomyelin and total sphingoid base. Ceramides and other sphingolipids play a major role in promoting cell differentiation and, thus, preventing, reducing, or eliminating skin dryness and wrinkles. Although several species of natural ceramides have been identified, these ceramides must be obtained through a lengthy process involving the extraction of ceramides from natural sources. Thus, the availability of natural ceramides is limited and their cost is very high. Several analogs of natural ceramides, known as pseudoceramides, have been synthesized. Pseudoceramides look similar but are not identical to ceramides. Unfortunately, pseudoceramides are still expensive, albeit not as expensive as natural ceramides.

Recent work has shown the ability of cultured keratinocytes to synthesize sphingolipids. Due to the high cost of natural or synthetic sphingolipids, cosmetic compositions which can enhance biosynthesis of sphingolipids are desirable, in order to minimize or eliminate the need for exogenous application of sphingolipids.

Skin treatment compositions are known which contain alpha hydroxy acids as ingredients for improving the appearance of dry, flaky, wrinkled, aged, photodamaged skin and for treating various disorders of skin, e.g., hyperkeratosis, ichthyosis, skin blemishes, acne, warts, herpes, psoriasis, eczema, pruritis.

PCT application WO 93/04669 discloses compositions containing N-acetyl-L-cysteine or derivatives thereof. The compositions are said to efface and prevent wrinkles in mammalian skin.

PCT Application WO 93/10755 discloses compositions containing salicylic acid as an essential ingredient in combination with an additional active component, which may be a N-acetyl-L-cysteine derivative. Many optional ingredients are disclosed, among which alpha hydroxy acids or derivatives thereof are mentioned. The compositions are said to regulate wrinkles and/or atrophy in mammalian skin.

The art discussed above does not address the need for increasing sphingolipid biosynthesis in skin and does not envision skin treatment compositions based on a specific lipid biosynthesis enhancing system of N-acetyl-L-cysteine and alpha hydroxy acid according to the present invention. The art does not teach or suggest that N-acetyl-L-cysteine is capable of enhancing lipid biosynthesis or that alpha hydroxy acids further compliment the action of N-acetyl-L-cysteine. It was found, as part of the present invention, that compositions according to the PCT application 93/10755 do not attain a statistically significant increase in lipid biosynthesis.

Accordingly, it is an object of the present invention to provide skin treatment compositions for increasing sphingolipid biosynthesis in mammalian skin.

It is another object of the invention to provide a composition for improving skin condition by improving water barrier performance.

It is another object of the present invention to provide compositions containing N-acetyl-L-cysteine and an alpha hydroxy acid (or a derivative of an alpha hydroxy acid) as an active system capable of increasing sphingolipid biosynthesis in mammalian skin, while tailoring the rest of the composition so as to minimize or substantially eliminate any blocking effect on the active system.

It is another object of the invention to provide a method for treating or preventing the appearance of wrinkled, flaky, aged, photodamaged skin or skin disorders.

It is yet another object of the invention to provide a method for enhancing lipid biosynthesis in mammalian skin.

It is another object of the invention to provide a method for improving skin condition by improving the performance of water barrier.

These and other objects of the invention will become more apparent from the detailed description and examples that follow.

SUMMARY OF THE INVENTION

The above objects are attained by the present invention which includes, in part, a skin treatment composition containing
 (i) a sphingolipid biosynthesis enhancing system consisting essentially of:
  a) an effective amount of an ingredient selected from the group consisting of an alpha hydroxy acid, a salt thereof, an ester thereof, and mixtures thereof;
  b) from about 0.001 to about 20% of N-acetyl-L-cysteine, and
 (ii) a cosmetically acceptable vehicle for the sphingolipid biosynthesis enhancing system;
wherein the composition is free of salicylic acid.

The invention is based, in part, on the discovery that a specific combination of actives enhances sphingolipid biosynthesis in skin. Although exogenously introduced N-acetyl-L-cysteine enhances sphingolipid biosynthesis even when used alone, alpha hydroxy acids, as keratinocyte proliferation agents, compliment the action of N-acetyl-L-cysteine by providing more cells for N-acetyl-L-cysteine to act on.

The invention also contains a discovery that salicylic acid blocks the beneficial effect on sphingolipid biosynthesis of the binary mixture of NAC and alpha hydroxy acid. Thus, according to the present invention, skin treatment compositions for the enhancement of lipid biosynthesis must be carefully tailored: the absence of salicylic acid in the inventive compositions is as critical as the presence of the lipid biosynthesis enhancement system, since if salicylic acid is present, the sphingolipid biosynthesis enhancing effect is substantially reduced or entirely obliterated.

The amount of alpha hydroxy acid is important in order to attain the lipid biosynthesis enhancement: if too little alpha hydroxy acid is used, no significant improvement may be attained over the action of N-acetyl-L-cysteine alone.

According to the present invention, by virtue of including an effective amount of alpha hydroxy acid into N-acetyl-L-cysteine containing compositions, and by virtue of avoiding the blocking effect of salicylic acid the performance of the compositions is substantially improved.

In the preferred embodiment of the invention, inventive compositions include L-isomers of alpha hydroxy acid, and/or dicarboxylic alpha hydroxy acids.

A further advantage of the present compositions is that lower levels of ceramides and/or other sphingolipids may be included in the composition containing sphingolipid biosynthesis enhancing system of the present invention to equal the performance of a similar formulation without the inventive system in order to minimize the cost of compositions.

The present invention also includes a method of improving or preventing the appearance of wrinkled, flaky, aged, photodamaged skin and treating skin disorders, which method includes applying to the skin a composition containing an active system based on a specific combination of alpha hydroxy acid and N-acetyl-L-cysteine.

Compositions of the invention are intended for topical application to mammalian skin which is already in dry, flaky, wrinkled, aged, photodamaged condition or which suffers from a skin disorder, or, in the alternative, the inventive compositions may be applied prophylactically to normal healthy skin to prevent or reduce dryness and the deteriorative changes.

DETAILED DESCRIPTION OF THE INVENTION

The first essential ingredient of the inventive composition is selected from the group consisting of an alpha hydroxy acid, a salt of an alpha hydroxy acid, an ester of an alpha hydroxy acid, and mixtures thereof. All the above listed suitable ingredients are collectively termed herein "alpha hydroxy acid."

The alpha hydroxy acid or its ester has the following structure:

$$R_2CHOHCOOR_1$$

wherein $R_1$ and $R_2$ are H, alkyl, aralkyl or aryl group of saturated or unsaturated, isomeric or non-isomeric, straight or branched chain or cyclic form, having 1 to 30 carbon atoms, and in addition $R_2$ may carry F, Cl, Br, I, N, S, OH, CHO, COOH and alkoxy group having 1 to 9 carbon atoms. The alpha hydroxy acids may be present as a free acid or an ester form, or in a salt form with an organic base or an inorganic alkali. The typical alkyl, aralkyl and aryl groups for $R_1$ and $R_2$ include methyl, ethyl, propyl, isopropyl, butyl, pentyl, octyl, lauryl, stearyl, benzyl and phenyl, etc.

D, DL, or L stereoisomeric forms of an alpha hydroxy acid may be employed in the inventive compositions.

Examples of suitable alpha hydroxy acids include but are not limited to:
 alpha hydroxy acetic acid (also known as "glycolic acid")
 alpha hydroxypropionic acid (also known as "lactic acid")
 alpha hydroxytetranoic acid
 alpha hydroxyhexanoic acid
 alpha hydroxyoctanoic acid (also known as "alpha hydroxy caprylic acid")
 alpha hydroxynonanoic acid
 alpha hydroxydecanoic acid
 alpha hydroxyundecanoic acid
 alpha hydroxydodecanoic acid (also known as "alpha hydroxy lauric acid")
 alpha hydroxytetradecanoic acid
 alpha hydroxyhexadecanoic acid
 alpha hydroxyoctadecanoic acid
 alpha hydroxyoctaeicosanoic acid;
dicarboxylic alpha hydroxy acids:
 dihydroxybutanedioic acid (tartaric acid)
 2-hydroxybutanedioic acid (malic acid)
 2-hydroxy propandioic acid
 2-hydroxy hexandioic acid
 2-hydroxy octanedioic acid
 2-hydroxy decandioic acid
 2-hydroxy dodecandioic acid
 2-hydroxy myristicdioic acid
 2-hydroxy palmiticdioic acid
Tricarboxylic alpha hydroxy acids:
 2-hydroxy-1,2,3,-propanetricarboxylic acid (citric acid)
 1-hydroxy-1,2,3,-propanetricarboxylic acid (isocitric acid)
and mixtures thereof.

Examples of suitable esters of alpha hydroxy acids include but are not limited to:
 alpha hydroxypropionic acid ethyl ester
 alpha hydroxypropionic acid propyl ester
 alpha hydroxytetranoic acid ethyl ester
 alpha hydroxyhexanoic acid methyl ester
 alpha hydroxyhexanoic acid ethyl ester
 alpha hydroxyoctanoic acid hexyl ester
 alpha hydroxyoctanoic acid methyl ester
 alpha hydroxyoctanoic acid ethyl ester
 alpha hydroxyoctanoic acid pentyl ester
 alpha hydroxyoctanoic acid octyl ester
 alpha hydroxyoctadecanoic acid ethyl ester
 alpha hydroxyoctanoic acid monoglyceride
 alpha hydroxyoctanoic acid diglyceride
 alpha hydroxyoctanoic acid triglyceride,
analogous esters of di- and tricarboxylic alpha hydroxy acids, and mixtures thereof.

Suitable salts of alpha hydroxy acids include but are not limited to sodium, potassium, ammonium, triethanolamine, calcium, lithium salts. The salts may be obtained commercially or they may be prepared by methods known in the art, e.g., neutralizing an alpha hydroxy acid with a suitable base, such as hydroxide bases of ammonium, potassium, sodium.

It has been found, as part of the present invention, that an L-form of alpha hydroxy acids is superior to the D-form of alpha hydroxy acid. Accordingly, in order to maximize performance at reduced levels of alpha hydroxy acids, in the most preferred embodiment of the invention, inventive compositions contain the L-form of an alpha hydroxy acid. Preferred compositions according to the invention contain at least 60% of an alpha hydroxy acid in L-configuration, by weight of total alpha hydroxy acid. Preferably, in order to attain optimum performance, the inventive compositions contain from 60% to more than 99%, most preferably more than 99% of alpha hydroxy acids by weight of total hydroxy acids in the composition is in the L-form.

In the most preferred embodiment of the invention a dicarboxylic alpha hydroxy acid is used, particularly tartaric, malic, especially the L-form thereof, due to the optimum performance of these acid in stimulating keratinocyte proliferation.

The total amount of alpha hydroxy acid in the inventive compositions ranges from 0.001% to 20%, preferably from 0.1% to 15% by weight of the composition, in order to attain maximum performance at optimal cost. In general, the more active is a particular alpha hydroxy acid in promoting keratinocyte proliferation, the less of it may be required to enhance the action of N-acetyl-L-cysteine.

Preferably, in order to attain a substantial benefit from the presence of N-acetyl-cysteine, the total concentration of alpha hydroxy acids in the inventive compositions is at least 1–5% by weight of the composition.

The second essential ingredient of inventive compositions is N-acetyl-L-cysteine ("NAC") of Formula I:

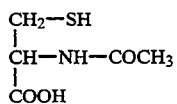

(I)

NAC is employed in the inventive compositions in the amount effective to enhance lipid biosynthesis. Generally, the amount is in the range of from 0.001% to 20%. The precise amount will depend on the particular alpha hydroxy acid included in the inventive compositions. Preferably, the amount is in the range of from 0.1% to 10% by weight of the composition, most preferably in the range of from 0.1% to 5% to attain maximum performance at optimal cost.

The ratio of NAC to alpha hydroxy acid is such as to obtain a complimentary action of AHA and NAC. The particular ratio will depend on the skin condition and the specific AHA employed. The ratio of alpha hydroxy acid to NAC is generally in the range of from 1:100 to 100:1, preferably 1:5 to 5:1.

The inventive compositions are free of salicylic acid. The absence of salicylic acid is critical in order to attain the sphingolipid biosynthesis enhancing benefit in the inventive compositions. Salicylic acid when used alone does not promote sphingolipid biosynthesis. When added to the sphingolipid biosynthesis enhancing system, salicylic acid substantially inhibits or eliminates the effect of the lipid biosynthesis enhancing system of the present invention. In this respect, it may be said that the inventive compositions consist essentially of the sphingolipid biosynthesis enhancing system as described above. The term "consists essentially of" means that the composition may include additional ingredients, but only if the additional ingredients do not materially alter the basic and novel characteristics of the claimed composition. The "consisting essentially of" language excludes the presence of salicylic acid.

The skin treatment composition of the invention also includes a therapeutically acceptable vehicle or a carrier which is inert, usually an ingredient present in highest amounts, and functioning to deliver active or performance ingredients. The amount of vehicle may range from about 2 to about 99%, preferably from about 5 to about 80%, most preferably from about 25 to 80%, by weight of the total compositions.

Surfactants, which are also sometimes designated as emulsifiers, may be incorporated into the cosmetic compositions of the present invention. Surfactants can comprise anywhere from about 0.5 to about 30%, preferably from about 1 to about 15% by weight of the total composition. Surfactants may be cationic, nonionic, anionic, or amphoteric in nature and combinations thereof may be employed.

Illustrative of the nonionic surfactants are alkoxylated compounds based upon fatty alcohols, fatty acids and sorbitan. These materials are available, for instance, from the Shell Chemical Company under the "Neodol" designation. Copolymers of polyoxypropylene-polyoxyethylene, available under the Pluronic trademark sold by the BASF Corporation, are sometimes also useful. Alkyl polyglycosides available from the Henkel Corporation similarly can be utilized for the purposes of this invention.

Anionic-type surfactants may include fatty acid soaps (polyglyceryl oleates), sodium lauryl sulphate, sodium lauryl ether sulphate, alkyl benzene sulphonate, mono and dialkyl acid phosphates and sodium fatty acyl isethionate.

Amphoteric surfactants include such materials as dialkylamine oxide and various types of betaines (such as cocoamido propyl betaine).

Emollients are often incorporated into cosmetic compositions of the present invention. Levels of such emollients may range from about 0.5 to about 50%, preferably between about 5 and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include isostearyl neopentanoate, 2-ethyl-hexyl myristate, isopropyl stearate and isostearyl palmitate. Acceptable tribasic acid esters include triisopropyl trilinoleate and trilauryl citrate. Acceptable straight chain fatty esters include cetyl octanoate lauryl palmitate, myristyl lactate, oleyl erucate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5 to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances, the thickening function may be accomplished by a material also serving as a silicone or emollient. For instance, silicone gums in excess of 10 centistokes and esters such as glycerol stearate have dual functionality.

Various types of active ingredients may be present in cosmetic compositions of the present invention. Actives are defined as skin benefit agents other than emollients and other than ingredients that merely improve the physical characteristics of the composition. Although not limited to this category, general examples include sunscreens, tanning agents, other skin anti-wrinkling agents, and anti-acne agents.

Ceramides and/or other sphingolipids may be included in the inventive composition, although inventive compositions enhance the sphingolipid (including ceramide) biosynthesis in skin. Suitable ceramides and synthetic analogues thereof are disclosed in European Patent Application 534 286, European Patent Application 227 994, U.S. Pat. No. 5,175,321, U.S. Pat. No. 4,985,547, U.S. Pat. No. 5,028,416, U.S. Pat. No. 5,071,971, Japanese Patent Application 63192703, U.S. Pat. No. 4,468,519, and U.S. Pat. No. 4,950,688, all of which are incorporated by reference herein. Sphingolipids, including ceramides or their synthetic analogues, may be present in the inventive compositions at a level of from about 0.00001 to about 5%, preferably from about 0.0001 to about 1%, optimally from about 0.01 to 0.5%.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the surfs UV radiation.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds.

Particularly preferred preservatives of this invention are methyl paraben, propyl paraben, imidazolidinyl urea, sodium dehydroxyacetate and benzyl alcohol. Preservatives will usually be employed in amounts ranging from about 0.5% to 2% by weight of the composition.

Other adjunct minor components may also be incorporated into the cosmetic compositions. These ingredients may include coloring agents, opacifiers and perfumes. Amounts of these materials may range anywhere from 0.001 up to 20% by weight of the composition.

The composition according to the invention is intended primarily as a product for topical application to human skin, especially as an agent for reducing the permeability to water of the skin, particularly when the skin is dry or damaged, in order to reduce moisture loss and generally to enhance the quality and flexibility of skin. The composition can also be applied to hair and nails.

The inventive compositions which include longer chain (i.e., more than 8 carbon atoms) mono- or di-alpha hydroxy acids have surfactant properties and can therefore also be used, in the form of a composition as herein defined, for cleansing the surface of the human body. In particular, the composition can be used to cleanse the skin to remove makeup or can be employed in a shampoo for cleansing the hair.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

The topical skin treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

EXAMPLES

EXAMPLE 1

Effect of Alpha Hydroxy Acids on Keratinocyte Proliferation

Keratinocyte proliferation (which is indicative of skin thickness and skin proliferative capacity) decreases with age. Thus, the increase in keratinocyte proliferation is beneficial to counteract skin aging (i.e., wrinkles, thickness, elasticity, and repair). According to the present invention, increased proliferation is beneficial because it provides more cells for N-acetyl-L-cysteine to act on to induce sphingolipid biosynthesis, resulting in enhanced sphingolipid biosynthesis.

Human keratinocytes were seeded at a relatively low density in wells of microtiter plates. The next day, cells were treated with various concentrations of a specific alpha hydroxy acid in keratinocyte basal medium containing 0.15 mM calcium. After 4 days of treatment the media was removed and the cells were lysed by repeated freeze thawing. The number of keratinocytes were determined by a fluorescent dye which binds to the cell's DNA. The amount of fluorescense is directly proportional to the number of cells present. Control cells were analyzed in the absence of any alpha hydroxy acids. The results that were obtained are summarized in Table 1 and indicate the response of the most effective concentration tested.

TABLE 1

|  | % INCREASE RELATIVE TO CONTROL |
|---|---|
| L-tartaric acid | 340* |
| L-malic acid | 360* |
| Citric acid | 135* |
| Glycolic acid | 122* |
| 2-Hydroxy octanoic acid | 127* |
| L-Lactic acid | 135* |

TABLE 1-continued

| | % INCREASE RELATIVE TO CONTROL |
|---|---|
| D-Lactic acid | 104 |

*significantly different from control

The data in Table 1 indicates that alpha hydroxy acids promote keratinocyte proliferation, and that the L-form of alpha hydroxy acid is significantly superior to the D-form in eliciting keratinocyte proliferation. Furthermore, dicarboxylic alpha hydroxy acids (i.e., L-tartaric, L-malic) are more potent promoters of proliferation than mono alpha hydroxy acids (i.e., citric, glycolic, lactic).

EXAMPLE 2

N-acetyl-L-cysteine, salicylic acid and DL-lactic acid are purchased from Sigma Chemical Co., St. Louis, Mo. Stock solutions of NAC, salicylic acid and lactic acid were made at 1.0M and pH adjusted to 7.0. Stock solutions were diluted into culture medium to the designated concentrations before the treatment. Keratinocyte culture medium is from GIBCO BRL. Grand Island, N.Y. $^{14}C$-acetate is from DuPont NEN Research Products. Boston, Mass.

Human keratinocytes were cultured in GIBCO Keratinocyte-SFM (serum-free keratinocyte medium containing 0.09 mM calcium chloride), 37° C., 5% $CO_2$ to confluent, treated with two components (lactic acid and NAC), and three components (Salicylic acid, lactic acid, and NAC) for 24 hours, respectively. The concentrations of chemicals used in this experiment were, salicylic acid, 0.5 mM; lactic acid, 0.5 mM; and NAC, 2.0 mM. $^{14}C$-acetate (10 $\mu$Ci/ml) was used to label epidermal lipids synthesized during the period of treatment. At the end of the incubation, cells were harvested and lipids were extracted using Bligh/Dyer method and subject to analysis on a standard TLC plate. The separated lipids on the plates were then quantified by Bioscan, system 200 imaging scanner. Specific epidermal lipids were identified by comparing with the lipid standards after charing of the plate.

The results that were obtained are summarized in Table 2.

TABLE 2

| TREATMENT | CERAMIDES % OF TOTAL COUNT | CERAMIDES % INCREASE/ CONTROL |
|---|---|---|
| Control | 4.26 | 0.0 |
| NAC + lactic acid (according to the invention) | 4.81 | 13.0 |
| NAC + lactic Acid + salicylic acid (according to PCT 93/10755) | 4.30 | 0.9 |

2.0 mM NAC
0.5 mM lactic acid
0.5 mM salicylic acid

The results in table 2 indicate that 13% of increase in ceramides biosynthesis was induced by the 24 hours period of treatment with the two components (lactic acid and NAC) within the scope of the invention as compared to the control. Almost no effect on ceramides level increase was observed from the three component treatment, which is not within the scope of the invention. The results indicate that combination of lactic acid and NAC stimulated keratinocyte ceramides biosynthesis at a substantially higher level as compared to the three component system.

EXAMPLE 3

This example illustrates a high internal phase water-in-oil emulsion incorporating the lipid biosynthesis enhancing composition of the invention.

| | % w/w |
|---|---|
| L-Tartaric acid | 5 |
| Fully hydrogenated coconut oil | 3.9 |
| N-acetyl cysteine | 0.1 |
| Brij 92* | 5 |
| Bentone 38 | 0.5 |
| Preservative | 0.3 |
| $MgSO_4 7H_2O$ | 0.3 |
| Butylated hydroxy toluene | 0.01 |
| Perfume | qs |
| Water | to 100 |

*Brij 92 is polyoxyethylene (2) oleyl ether

EXAMPLE 4

This example illustrates an oil-in-water cream incorporating the inventive composition.

| | % w/w |
|---|---|
| L-Lactic acid | 10 |
| Mineral oil | 4 |
| N-acetyl cysteine | 1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 5

This example illustrates an alcoholic lotion incorporating the composition according to the invention.

| | % w/w |
|---|---|
| 2-hydroxy octanoic acid | 1 |
| N-acetyl cysteine | 0.2 |
| Ethanol | 40 |
| Perfume | qs |
| Butylated hydroxy toluene | 0.01 |
| Water | to 100 |

EXAMPLE 6

This example illustrates another alcoholic lotion containing the inventive composition.

| | % w/w |
|---|---|
| N-acetyl cysteine | 0.2 |
| Dimethylsulphoxide | 10 |
| Ethanol | 40 |
| Antioxidant | 0.1 |
| Perfume | qs |
| Water | to 100 |

EXAMPLE 7

This example illustrates a suncare cream incorporating the lipid enhancement system of the invention:

|  | % w/w |
|---|---|
| L-Lactic acid | 5 |
| N-acetyl Cysteine | 1 |
| Ceramide-1 | 0.01 |
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 8

This example illustrates a non-aqueous skin care composition incorporating the inventive combination.

|  | % w/w |
|---|---|
| Tartaric acid | 5 |
| N-acetyl cysteine | 0.1 |
| Silicone gum SE-30[1] | 10 |
| Silicone fluid 345[2] | 20 |
| Silicone fluid 344[3] | 55.79 |
| Squalene | 10 |
| Ceramides | 0.01 |
| Linoleic acid | 0.01 |
| Cholesterol | 0.03 |
| 2-hydroxy-n-octanoic acid | 0.7 |
| Vitamin A palmitate | 0.5 |
| Vitamin E linoleate | 0.5 |
| Herbal oil | 0.5 |
| Ethanol | 2 |

[1] A dimethyl silicone polymer having a molecular weight of at least 50,000 and a viscosity of at least 10,000 centistokes at 25° C., available from GEC
[2] Dimethyl siloxane cyclic pentamer, available from Dow Corning Corp.
[3] Dimethyl siloxane tetramer, available from Dow Corning Corp.

What is claimed is:

1. A skin treatment composition comprising
   (i) a system for enhancing a sphingolipid biosynthesis in mammalian skin, the system consisting essentially of:
      a) from about 0.001 to about 20% of L-lactic acid. or a salt thereof; and
      b) from about 0.001 to about 20% of N-acetyl-L-cysteine; and
   (ii) a cosmetically acceptable vehicle for the sphingolipid biosynthesis enhancing system;
   wherein the composition is free of salicylic acid.

2. The composition of claim 1 wherein the amount of ingredient (b) is at least 0.1%.

3. The composition of claim 1 wherein the weight ratio of (a) to (b) is in the range of from 1:100 to 100:1.

4. A skin treatment composition for enhancing lipid biosynthesis in mammalian skin, the composition consisting essentially of
   a) from 0.001% to 20% of N-acetyl-L-cysteine, and
   b) from about 0.001 to about 20% of L-lactic acid, or a salt thereof.

5. A method of improving the appearance of wrinkled, flaky, or aged skin, the method comprising applying to the skin the composition of claim 1.

6. A method of enhancing ceramide biosynthesis in keratinocytes, the method comprising applying topically to the skin the composition of claim 1.

* * * * *

UNITED STATES PATENT AND TRADEMARK OFFICE
CERTIFICATE OF CORRECTION

PATENT NO. : 5,451,405
DATED : September 19, 1995
INVENTOR(S) : Zhang et al.

It is certified that error appears in the above-indentified patent and that said Letters Patent is hereby corrected as shown below:

Item [57]

The Abstract is replaced to read as follows:

-- Skin treatment compositions containing a system for enhancing sphingolipid production in skin containing N-acetyl-L-cysteine and an alpha hydroxy acid (or a salt, or an ester thereof). --

Signed and Sealed this

Twenty-sixth Day of March, 1996

Attest:

BRUCE LEHMAN

*Attesting Officer*  *Commissioner of Patents and Trademarks*